United States Patent
Christmann

(10) Patent No.: US 9,399,092 B2
(45) Date of Patent: Jul. 26, 2016

(54) DEVICE FOR THE REMOVAL OF SUBSTANCES FROM LIQUIDS IN PARTICULAR BLOOD

(75) Inventor: Horst Christmann, Usingen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 856 days.

(21) Appl. No.: 11/884,341

(22) PCT Filed: Feb. 1, 2006

(86) PCT No.: PCT/EP2006/000885
§ 371 (c)(1),
(2), (4) Date: Aug. 15, 2007

(87) PCT Pub. No.: WO2006/087103
PCT Pub. Date: Aug. 24, 2006

(65) Prior Publication Data
US 2008/0185322 A1    Aug. 7, 2008

(30) Foreign Application Priority Data

Feb. 17, 2005   (DE) .......................... 10 2005 007 372

(51) Int. Cl.
| | |
|---|---|
| *B01D 35/00* | (2006.01) |
| *B01D 35/26* | (2006.01) |
| *A61M 1/34* | (2006.01) |
| *A61M 1/30* | (2006.01) |

(52) U.S. Cl.
CPC ............. *A61M 1/3472* (2013.01); *A61M 1/303* (2014.02); *A61M 1/3417* (2014.02); *A61M 1/3486* (2014.02)

(58) Field of Classification Search
CPC . A61M 1/303; A61M 1/3417; A61M 1/3472; A61M 1/3486
USPC .............................................................. 702/45
See application file for complete search history.

(56) References Cited

U.S. PATENT DOCUMENTS

| | | | |
|---|---|---|---|
| 3,506,126 A | | 4/1970 | Serfass et al. |
| 3,669,880 A | * | 6/1972 | Marantz ............... A61M 1/1696 210/195.2 |
| 5,536,412 A | * | 7/1996 | Ash ................................ 210/645 |

(Continued)

FOREIGN PATENT DOCUMENTS

| | | |
|---|---|---|
| DE | 2 152 355 | 4/1973 |
| DE | 41 13 185 C1 | 7/1992 |
| DE | 43 38 858 C1 | 4/1995 |
| DE | 199 17 522 A1 | 10/2000 |
| EP | 0 472 480 B1 | 2/1992 |

(Continued)

OTHER PUBLICATIONS

Machine Translation of Foreign Patent Document DE 43 38 858 Kastl.*

*Primary Examiner* — Dirk Bass
(74) *Attorney, Agent, or Firm* — Jacobson Holman, PLLC

(57) ABSTRACT

The invention relates to an apparatus for the elimination of substances from liquids, in particular from blood, comprising a primary circuit for the liquid to be treated, a filter which is integrated therein and at whose secondary side a secondary circuit is connected in which at least one adsorber is arranged, wherein respective pumps are provided in the primary and secondary circuits. In accordance with the invention, an expansion vessel in which liquid of the secondary circuit is discontinuously taken up and output again is integrated in the secondary circuit.

25 Claims, 2 Drawing Sheets

(56) References Cited

U.S. PATENT DOCUMENTS

| | | | |
|---|---|---|---|
| 5,855,782 A | 1/1999 | Falkenhagen et al. | |
| 6,526,357 B1 * | 2/2003 | Soussan et al. | 702/45 |
| 2003/0069559 A1 * | 4/2003 | Platt et al. | 604/500 |
| 2004/0186407 A1 | 9/2004 | Walker et al. | |

FOREIGN PATENT DOCUMENTS

| | | | |
|---|---|---|---|
| EP | 0 776 223 B1 | 6/1997 | |
| GB | 1 374 159 | 11/1974 | |
| JP | 401192368 * | 8/1989 | 210/645 |
| WO | WO 95/18671 | 7/1995 | |

* cited by examiner

DEVICE FOR THE REMOVAL OF SUBSTANCES FROM LIQUIDS IN PARTICULAR BLOOD

CROSS-RELATED TO RELATED APPLICATION

This is a National stage of PCT/EP2006/000885 filed Feb. 1, 2006 and published in German.

BACKGROUND OF THE INVENTION

1. Field of Invetion

The invention relates to an apparatus for the elimination of substances from liquids, in particular from blood.

2. Description of the Prior Art

Blood treatment devices are already known in which blood is first guided into a primary extracorporeal circuit through a hemodialyzer or a hemofilter. The second chamber of the filter is part of a secondary circuit in which only specific components of the blood are circulated. The actual blood treatment elements such as adsorber elements are provided in this secondary circuit. The split into two circuits can be necessary if the adsorber elements should not come into contact with the full blood, but with the blood plasma.

Such an apparatus is, for example, already known from EP 0 776 223 B1. Here, a primary circuit for the liquid to be treated is present with a filter integrated therein. A secondary circuit in which at least one adsorber is arranged is connected to the secondary side of the filter.

A corresponding apparatus as described in FIG. 1 is known. A primary circuit 12 is shown there in which the liquid of the primary circuit, for example blood, is circulated by the pump 16. A filter 10 is integrated in the primary circuit. A secondary circuit 14 in which the liquid of the secondary circuit is circulated at a constant volume via a roller pump 18 adjoins the secondary side of the filter 10. Two adsorber elements 38 and 40 for the purification of the liquid of the secondary circuit 14 are integrated in the circuit. With this arrangement, a specific pressure gradient is adopted in the hemofilter, with an infusion of secondary liquid into the blood circuit taking place in the upper part of the filter (inlet of the secondary liquid) and a removal of liquid from the blood circuit taking place at the lower end (outlet of the secondary liquid). The replaced volumes balance precisely due to the constant volume. It is, however, a disadvantage that the absolutely replaced liquid volume, and thus the purified liquid volume, is not precisely defined.

Whereas the detoxification of blood is possible with serious liver failure using the filter 10, a hemodialyzer 42 can additionally be arranged in the primary circuit, as shown in FIG. 1 in accordance with the prior art, by means of which hemodialyzer water soluble toxins can be removed from the blood with the help of a dialysis machine via the extracorporeal blood circuit.

SUMMARY OF THE INVENTION

It is the object of the invention to make possible a precise detection of the replaced volumes in the secondary circuit.

This object is solved in accordance with the invention by the combination of the features of claim 1. Accordingly, in accordance with the invention, an expansion vessel is integrated in the secondary circuit, in which expansion vessel liquid of the secondary circuit can be discontinuously taken up and output again. In this solution, the invention makes use of the principle of so-called "single-needle" systems such as are known from EP 0 472 480 B1. In such methods, the access to the patient is established by a single cannula by which blood is alternately sucked in and put back. This requires the intermediate storage of blood in an expansion vessel. Within the framework of the present invention, no "single-needle" system is used, but rather an expansion vessel into which liquid is sucked or pressed through the filter in a first phase is integrated in the secondary circuit. In a second, subsequent phase, the liquid is then returned to the blood from the expansion vessel via the at least one filter. Since either an infusion into the blood or a filtration out of the blood takes place in the filter in dependence on the cycle and since the delivery rates in the secondary circuit are precisely known, the replaced liquid volumes can be recorded precisely and so balanced. A specific filtrate flow can be preset by the user with the apparatus proposed here. For instance, a substantially lower throughflow volume flow can be selected here so that the dwell time of the secondary liquid in the blood treatment elements, i.e. the adsorbers, for example, is larger, whereby the degree of adsorption of toxins is possibly improved.

Further details and advantages of the invention result from the dependent claims following the main claim.

Advantageously, valves can be provided in the secondary circuit for the distribution of the liquid of the secondary circuit in the discontinuous filling and emptying of the expansion vessel.

In accordance with another advantageous aspect of the invention, the filling level of the expansion vessel can be detected by a pressure sensor.

Modules from so-called "single-needle" systems can be made use of for the pump of the secondary circuit, with the pressure sensor being integrated. Blood can circulate in the primary circuit and plasma in the secondary circuit. In this application, a hollow fiber membrane filter (e.g. on a polysulfonic base) can preferably be used as the filter. It serves the separation of the plasma from the blood, with the membrane filter being permeable for albumin and substances having a low molecular weight.

In addition, a hemodialyzer for the simultaneous dialysis treatment can advantageously be integrated in the primary circuit. Water-soluble toxins are then removed from the blood using the dialysis treatment with the aid of the dialysis machine via the extracorporeal blood circuit. On liver failure, these insoluble toxins, which accumulate in the patient's blood and which are bound to proteins, usually to albumin, are separated by the secondary circuit in accordance with the present apparatus and here in particular by the adsorption.

BRIEF DESCRIPTION OF THE DRAWINGS

Further features, details and advantages of the invention result from an embodiment shown in the drawing. There are shown.

DETAILED DESCRIPTION OF THE PREFERRED EMBODIMENTS

Figure 1:
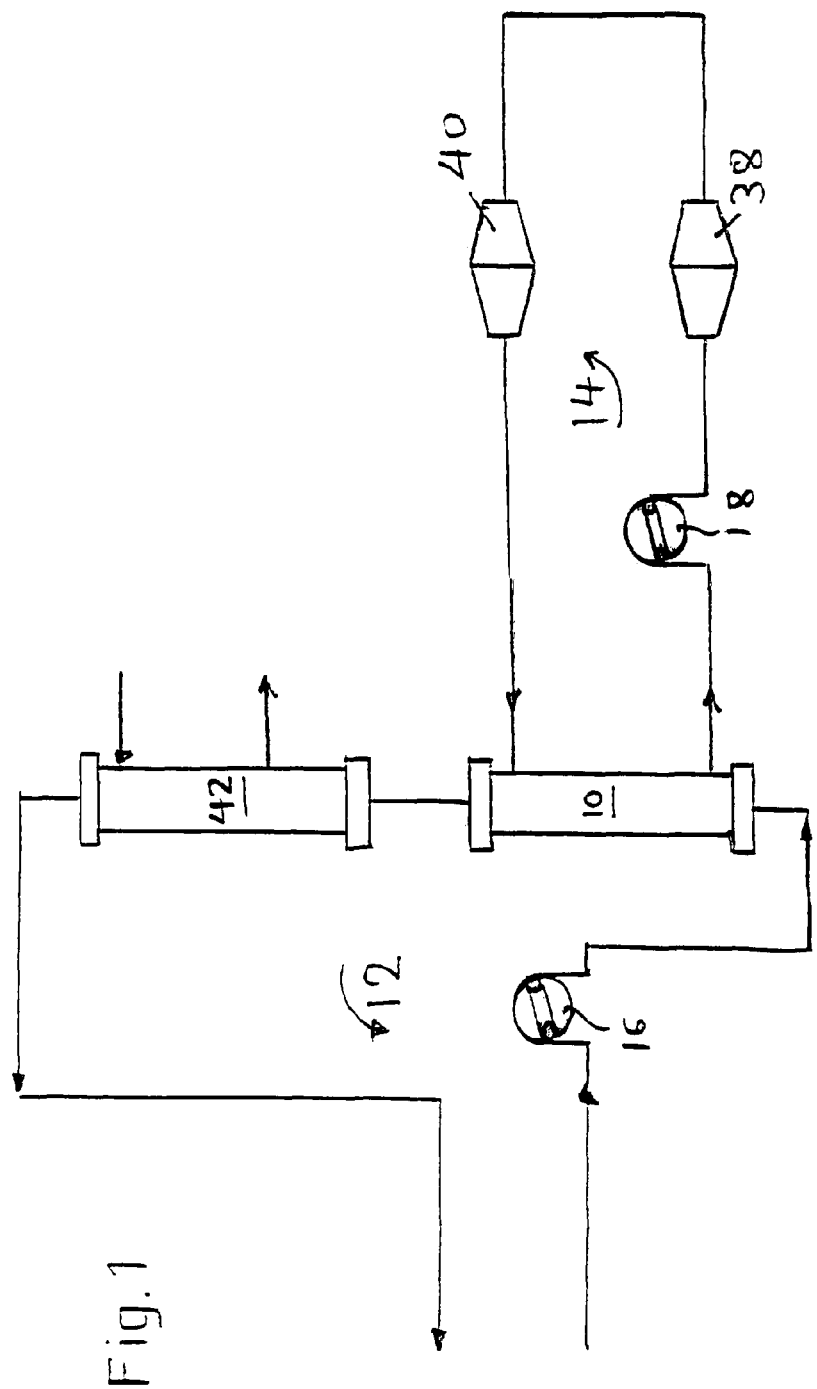
FIG. 1: an apparatus for the elimination of substances from blood in accordance with the prior art.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The apparatus in accordance with the invention of FIG. 2 comprises a primary circuit 12 in which patient blood is conveyed via a pump 16. In the primary circuit 12, a filter 10 is integrated which is configured as a membrane filter made of polysulfone. A secondary circuit 14 adjoins the membrane filter 10 and a pump 18 configured as a roller pump serves in it for the conveying of the plasma conveyed in this secondary circuit. Two adsorbers 38 and 40 are provided within the secondary circuit and protein-bound and so water-insoluble toxins can be removed via them by adsorption from the plasma.

Figure 2:
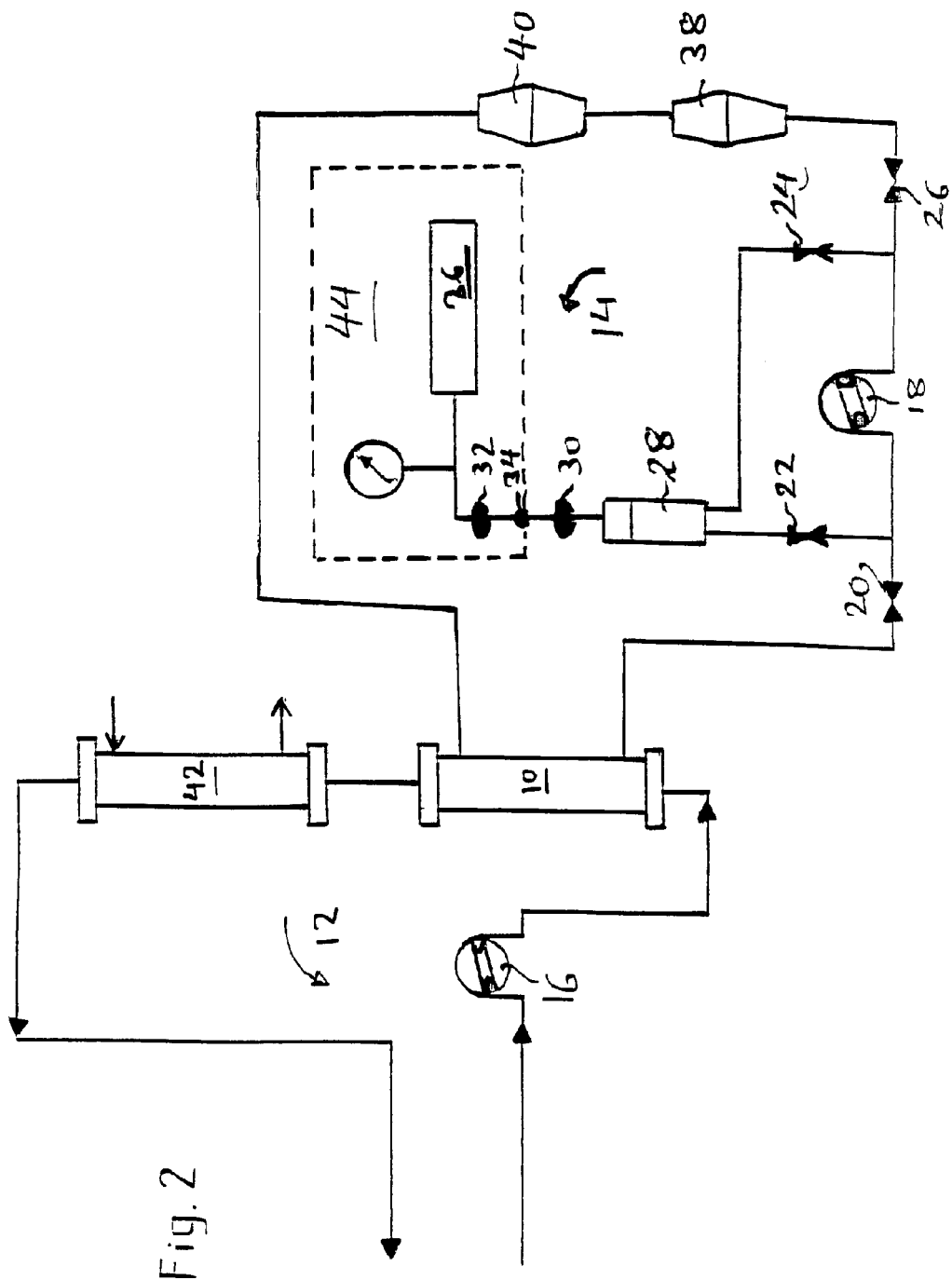
FIG. 2: an embodiment of the apparatus in accordance with the invention for the elimination of substances from blood.

In the secondary circuit 14, an expansion vessel 28 is integrated in which liquid of the secondary circuit 14, that is plasma, can be discontinuously taken up and output again. Valves 20, 22 and 24, 26 are provided for the distribution of the liquid of the secondary circuit on the discontinuous filling and emptying of the expansion vessel 28. The pump 18 is arranged between the valves 20 and 22, on the one hand, and 24 and 26, on the other hand, as shown in FIG. 2. The expansion vessel is furthermore in communication with a pressure sensor 44, with the pressure sensor being able to be an integrated component of the pump such as are already used in modular form in "single-needle" systems.

Hydrophobic filters 30 and 32 and a pressure measuring connection 34 are present here. A balance vessel is designated by 36. The plasma flow can be controlled by means of the pressure sensor 44.

The procedure of the individual discontinuous cycles results as follows: first, the valves 20 and 24 are opened, whereas the valves 22 and 26 are closed. The pump 18 in this state sucks in fresh plasma via the filter 10 and conveys it into the expansion vessel 28 until the upper switching pressure is reached. The switching pressure is measured by the pressure sensor 44. Subsequently, the valves 22 and 26 are opened, whereas the valves 20 and 24 are closed. In this case, the plasma is conveyed out of the expansion vessel 28 and is supplied back to the filter 10 and thus to the primary circuit after flowing through the adsorbers 38 and 40. An accurately defined filtrate volume flow amount can hereby be set. In a common system, the volume flow amounts to 20 to 50 ml/min. The dwell time of the plasma in the adsorbers is thus comparatively larger. The adsorption of toxins can thereby be improved.

Alternatively, the system can be operated, as was already known from the prior art, at a relatively high recirculation flow on the plasma side. For this purpose, the valves 20 and 26 are open, whereas the valves 22 and 24 are closed. A plasma volume flow in the order of magnitude of 300 ml/min can be realized here in comparison with the aforesaid volume flows.

The filter 10 comprises a membrane filter of polysulfone which is permeable for albumin and substances with a low molecular weight. It serves for the separation of the patient's plasma from the blood. In the secondary circuit, as previously described in detail, a plasma separation is carried out by means of adsorption for the removal of the protein-bound toxins.

In addition, a dialysis treatment can be carried out via a hemodialyzer 42 in the primary circuit, via which dialysis treatment the water-soluble toxins are removed from the blood via the extracorporeal blood circuit with the aid of a dialysis machine not shown in any more detail here.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. An apparatus for eliminating substances from a liquid, in particular from blood, said apparatus comprising:
   a primary circuit in which the liquid is treated;
   a filter integrated in the primary circuit, said filter having a secondary side that is a part of a closed secondary circuit in which at least one liquid treatment element that is an adsorber is arranged, the adsorber being a sorbent cartridge or equivalent, with respective pumps being provided in the primary and secondary circuits, the filter separating the primary circuit and the closed secondary circuit from each other, and the secondary side of the filter being directly connected to the closed secondary circuit;
   an expansion vessel integrated in the secondary circuit, said expansion vessel being configured to take up a liquid of the secondary circuit from the filter in a first phase and then output the liquid of the secondary circuit back to the filter after the secondary circuit liquid has flowed through the adsorber in a second phase;
   a first line and a second line of the secondary circuit, the first line and the second line each being connected to the filter, with the expansion vessel being arranged between the first line and the second line of the secondary circuit, and with the adsorber being integrated in the second line;
   a secondary circuit pump connected to the first line and the second line in parallel with the expansion vessel; and
   an outlet line of the expansion vessel, the first line, and a first side of the secondary circuit pump being connected in a first connection point, and an inlet line of the expansion vessel, the second line, and a second side of the secondary circuit pump being connected in a second connection point.

2. The apparatus in accordance with claim 1, further comprising valves present in the secondary circuit for the distribution of the liquid of the secondary circuit in filling and emptying of the expansion vessel.

3. An apparatus in accordance with claim 1, further comprising a pressure sensor to detect a filling level of the expansion vessel.

4. The apparatus in accordance with claim 3, wherein the pump of the secondary circuit and the pressure sensor are integrated in a module.

5. The apparatus in accordance with claim 1, wherein the primary circuit is configured to circulate the blood and the secondary circuit is configured to circulate plasma.

6. The apparatus in accordance with claim 5, wherein the filter is a membrane filter having a polysulfone construction.

7. The apparatus in accordance with claim 1, further comprising a hemodialyzer integrated in the primary circuit for a simultaneous dialysis treatment.

8. The apparatus according to claim 1, further comprising a pressure sensor that controls the flow of the liquid of the secondary circuit by (i) sensing a pressure in the expansion vessel and (ii) switching operation between the first phase and the second phase based on the sensed pressure.

9. The apparatus according to claim 8, further comprising a first pair of second circuit valves and a second pair of second circuit valves that are controlled by the sensed pressure of the pressure sensor so as to switch the operation between the first phase and the second phase.

10. The apparatus according to claim 1, wherein the secondary circuit pump conveys the liquid of the secondary circuit.

11. The apparatus according to claim 1, wherein the apparatus is configured such that in the first phase, liquid flows from the filter via the first line to the expansion vessel, and in the second phase, liquid flows from the expansion vessel via the second line and the adsorber arranged therein to the filter.

12. The apparatus according to claim 11, wherein the apparatus is configured such that in the first phase, liquid flow through the second line is blocked, and in the second phase, liquid flow through the first line is blocked.

13. The apparatus according to claim 1, wherein the apparatus is configured such that in the first phase, the secondary circuit pump draws liquid from the filter via the first line and pumps the liquid to the expansion vessel, and in the second phase, the secondary circuit pump draws liquid from the expansion vessel and pumps the liquid drawn therefrom via the second line and adsorber arranged therein to the filter.

14. The apparatus according to claim 1, wherein the apparatus is configured such that in the first phase, the secondary circuit pump draws the liquid from the filter via the first line, the first connection point, and the first side of the secondary circuit pump, and pumps the liquid to the expansion vessel via the second side of the secondary circuit pump, the second connection point and the inlet line, and in the second phase, the secondary circuit pump draws liquid from the expansion vessel via the outlet line, the first connection point, and the first side of the secondary circuit pump, and pumps the drawn liquid from the second side of the secondary circuit pump via the second connection point, the second line, the adsorber, and a third line to the filter.

15. The apparatus according to claim 1, further comprising a valve arranged in the inlet line of the expansion vessel, a valve arranged in the outlet line of the expansion vessel, a valve arranged in the first line, and a valve arranged in the second line.

16. The apparatus in according to claim 1, wherein the adsorber is a sorbent cartridge.

17. The apparatus according to claim 1, wherein the apparatus is configured such that in the first phase, the liquid taken up in the expansion vessel is extracted from the primary circuit via a membrane of the filter, and in the second phase, the liquid output from the expansion vessel is reintroduced into the primary circuit via the membrane.

18. The apparatus according to claim 17, wherein the apparatus is configured such that the liquid is extracted from the primary circuit via the membrane of the filter, and in the second phase, the liquid output from the expansion vessel is reintroduced into the primary circuit.

19. An apparatus for eliminating substances from a liquid, comprising:
  a primary circuit for treating the liquid, the primary circuit including a pump;
  a secondary circuit;
  a filter having a primary side and a secondary side separated by a membrane, the filter being integrated in the primary circuit with the primary side thereof and integrated in the secondary circuit with the secondary side thereof, such that the membrane of the filter separates the primary circuit and the secondary circuit;
  an adsorber integrated in the secondary circuit, the adsorber being a sorbent cartridge or equivalent;
  an expansion vessel integrated in the secondary circuit, the expansion vessel being connected to the filter by the secondary circuit,
  with the expansion vessel, in a first phase, configured to take up a liquid flowing in the secondary circuit from the filter to the expansion vessel, the liquid being extracted in the filter from the first circuit via the membrane into the secondary circuit, and, in a second phase, configured to output the liquid, the liquid flowing in the secondary circuit back to the filter, where the liquid is reintroduced from the secondary circuit into the primary circuit via the membrane, and
  the adsrober being arranged in the secondary circuit at a position between the filter and the expansion vessel, such that the liquid extracted form the first circuit flows through the adsorber before the liquid is reintroduced into the primary circuit;
  in the secondary circuit, a first line and a second line, with the secondary side of the filter being connected to the first line and the second line of the secondary circuit, and the expansion vessel being arranged between the first line and the second line of the secondary circuit, and with the adsorber being arranged in the first line or the second line;
  a secondary circuit pump arranged between the first line and the second line in parallel with the expansion vessel, wherein in the first phase, the secondary circuit pump draws the liquid from the filter via the first line and pumps the liquid to the expansion vessel, and in the second phase, the secondary circuit pump draws the liquid form the expansion vessel and pumps the liquid via the second line to the filter; and
  an outlet line of the expansion vessel, the first line, and a first side of the secondary circuit pump being connected in a fist connection point, and an inlet line of the expansion vessel, the second line, and a second side of the secondary circuit pump being connected in a second connection point.

20. The apparatus according to claim 19, wherein the apparatus is configured such that in the first phase, liquid flow through the second line is blocked, and in the second phase, liquid flow through the first line is blocked.

21. The apparatus according to claim 19, wherein the apparatus is configured such that in the first phase, the secondary circuit pump draws the liquid from the filter via the first line, the first connection point, and the first side of the secondary circuit pump, and pumps the liquid to the expansion vessel via the second side of the secondary circuit pump, the secondary connection point, and the inlet line, and in the second phase, the secondary circuit pump draws the liquid from the expansion vessel via the outlet line, the first connection point, and the first side of the secondary circuit pump, and pumps the liquid from the secondary side of the secondary circuit pump via the second connection point and the second line to the filter.

22. The apparatus according to claim 19, further comprising a valve arranged in the inlet line of the expansion vessel, a valve arranged in the outlet line of the expansion vessel, a valve arranged in the first line, and a valve arranged in the second line.

23. The apparatus according to claim 19, wherein the adsorber is a sorbent cartridge.

24. The apparatus according to claim 1, wherein the apparatus is configured such that in the second phase, the liquid continuously flows from the expansion vessel through the adsorber to the filter.

25. The apparatus according to claim 19, wherein the apparatus is configured such that in the second phase, the liquid continuously flows from the expansion vessel through the adsorber to the filter.

* * * * *